United States Patent [19]

Petrillo, Jr.

[11] 4,396,772
[45] Aug. 2, 1983

[54] PHOSPHINYLALKANOYL AMINO ACIDS

[75] Inventor: Edward W. Petrillo, Jr., Pennington, N.J.

[73] Assignee: F. R. Squibb & Sons, Inc., Princeton, N.J.

[21] Appl. No.: 323,859

[22] Filed: Nov. 23, 1981

[51] Int. Cl.³ .............................................. C07F 9/32
[52] U.S. Cl. .................... 548/414; 260/942; 260/943; 260/502.5 G; 548/112
[58] Field of Search ............... 260/943, 502.5 G, 942; 548/414, 112

[56] References Cited

U.S. PATENT DOCUMENTS

| | | | |
|---|---|---|---|
| 4,105,776 | 8/1978 | Ondetti et al. | 424/274 |
| 4,112,119 | 9/1978 | Ondetti et al. | 424/317 |
| 4,168,267 | 9/1979 | Petrillo | 424/274 |
| 4,179,464 | 12/1979 | Schultz et al. | 260/942 |
| 4,316,896 | 2/1982 | Thorsett et al. | 548/414 |
| 4,371,526 | 1/1983 | Rovnyak | 548/112 |

FOREIGN PATENT DOCUMENTS 9183  4/1980  European Pat. Off. .

*Primary Examiner*—Anton H. Sutto
*Attorney, Agent, or Firm*—Lawrence S. Levinson; Donald J. Barrack

[57] ABSTRACT

Angiotensin converting enzyme activity is inhibited by compounds having the formula

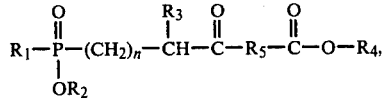

and salts thereof wherein $R_1$ is alkyl, aryl, arylalkyl, cycloalkyl, or cycloalkyl(alkyl);

$R_2$ and $R_4$ each is independently hydrogen, alkyl, arylalkyl or

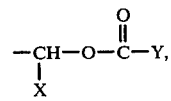

wherein X is hydrogen, alkyl, or phenyl and Y is hydrogen, alkyl, phenyl or alkoxy, or together X and Y are $-(CH_2)_2-$, $-(CH_2)_3-$, $-CH=CH-$ or

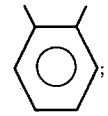

$R_3$ is hydrogen or alkyl;

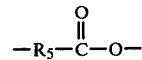

is a residue of an amino acid selected from the group consisting of glycine, alanine, valine, norvaline, leucine, N-methylleucine, norleucine, isoleucine, phenylalanine, tyrosine, serine, threonine, cysteine, methionine, aspartic acid, glutamic acid, arginine, lysine, asparagine, glutamine, histidine, or tryptophane; and
n is 0 or 1.

11 Claims, No Drawings

PHOSPHINYLALKANOYL AMINO ACIDS

RELATED APPLICATION

United States patent application No. 212,911, filed Dec. 4, 1980, now U.S. Pat. No. 4,337,201, issued June 29, 1982 discloses that phosphinylalkanoyl substituted prolines and esters of phosphinylalkanoyl prolines are inhibitors of angiotensin converting enzyme and are useful in the treatment of hypertension.

BACKGROUND OF THE INVENTION

The recent literature disclosed a variety of mercaptoacyl amino acids which are useful for inhibiting the conversion of angiotensin I to angiotensin II in mammals and are, therefore, useful in the treatment of hypertension. Also disclosed for the same utility are phosphinyl alkanoyl prolines.

United States Pat. No. 4,105,776, issued Aug. 8, 1978 discloses mercaptoacyl amino acids wherein the amino acid is, inter alia, proline, 4-hydroxyproline and 4-alkylproline.

U.S. Pat. No. 4,112,119 discloses mercaptoacyl amino acids wherein the amino acid is, inter alia, alanine, leucine, phenylalanine, arginine, sarcosine, serine, asparagine, lysine, histidine, glycine, tryptophane, cysteine, methionine, valine, glutamine, or tyrosine.

U.S. Pat. No. 4,168,267, issued Sept. 18, 1979 discloses phosphinylalkanoyl prolines, and esters and salts thereof.

BRIEF DESCRIPTION OF THE INVENTION

Compounds having the formula

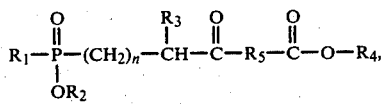

and salts thereof, have hypotensive activity. In formula I, and throughout the specification, the symbols are as defined below.

R₁ is alkyl, aryl, arylalkyl, cycloalkyl, or cycloalkyl(alkyl);

R₂ and R₄ each is independently hydrogen, alkyl, arylalkyl or

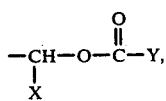

wherein X is hydrogen, alkyl, or phenyl and Y is hydrogen, alkyl, phenyl or alkoxy, or together X and Y are —(CH₂)₂—, —(CH₂)₃—, —CH=CH— or

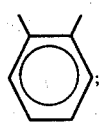

R₃ is hydrogen or alkyl;

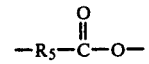

is a residue of an amino acid selected from the group consisting of glycine, alanine, valine, norvaline, leucine, N-methylleucine, norleucine, isoleucine, phenylalanine, tyrosine, serine, threonine, cysteine, methionine, aspartic acid, glutamic acid, arginine, lysine, asparagine, glutamine, histidine, or tryptophane; and n is 0 or 1.

The term "aryl," as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl," as used throughout the specification either by itself or as part of a larger group, refers to groups having 1 to 10 carbon atoms. Alkyl groups having 1 to 4 carbon atoms are preferred.

The term "cycloalkyl," as used throughout the specification either by itself or as part of a larger group, refers to groups having 3 to 7 carbon atoms.

The term "alkoxy," as used throughout the specification either by itself or as part of a larger group, refers to groups having 1 to 8 carbon atoms. Alkoxy groups having 1 to 3 carbon atoms are preferred.

The term "halogen," as used throughout the specification either by itself or as part of a larger group, refers to fluorine, chlorine, bromine and iodine. The preferred halogen groups are fluorine and chlorine.

The term "alkanoyl," as used throughout the specification either by itself or as part of a larger group, refers to groups having 2 to 9 carbon atoms.

DETAILED DESCRIPTION OF THE INVENTION

The compounds of formula I, and salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseduoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)-→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The phosphinylalkanoyl amino acids of formula I can be prepared by reacting a compound having the formula

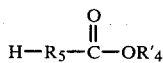

II with a phosphinyl-acetic or propionic acid having the formula

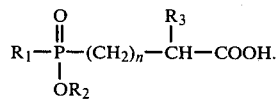

III

In formula II and throughout the specification, $R_4'$ is alkyl, arylalkyl or

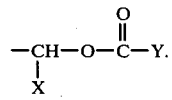

The reaction can be accomplished using known amide bond forming procedures. For example, the reaction can be run in the presence of a coupling agent such as dicyclohexylcarbodiimide, or the acid of formula III can be activated by formation of its mixed anhydride, symmetrical anhydride, acid halide (preferably acid chloride) or acid ester, or by the use of Woodward reagent K, N-ethoxycarbonyl-2-ethoxy-1,2-dihydroquinoline, N,N'-carbonyldiimidazole or the like. A review of these methods can be found in *Methoden er Organischen Chemie* (Houben-Weyl), Vol. XV, part II, page 1 et seq. (1974). The product of the reaction has the formula

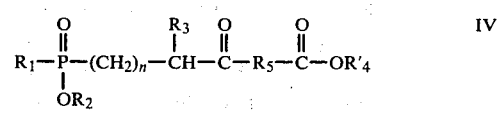

IV

Compounds of formula I wherein $R_2$ is hydrogen can alternatively by obtained by (i) treating a corresponding compound of formula IV wherein $R_2$ is alkyl with a halosilane such as bromotrimethylsilane and then water or (ii) catalytic hydrogenation of a corresponding compound of formula IV wherein $R_2$ is arylalkyl, e.g., using palladium on charcoal. These products have the formula

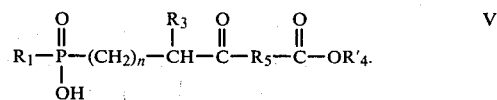

V

Compounds of formula I wherein $R_4$ is hydrogen, i.e., compounds having the formula

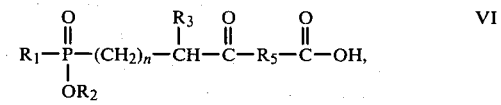

VI can be obtained by basic hydrolysis of a compound of formula IV or V. Alternatively, a compound of formula IV or V wherein $R_4'$ is an easily removable ester group (such as t-butyl) can be treated with trifluoroacetic acid and anisole to obtain the carboxylic acids of formula I.

The phosphinylalkanoyl amino acids of formula I wherein n is 1 can alternatively be prepared by reacting a compound of formula II with a phospholane having the formula

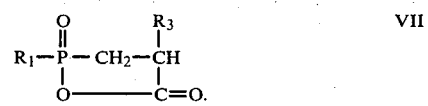

VII

The reaction proceeds most readily when run in the presence of an organic base, e.g., triethylamine, pyridine, N,N-dimethylamine or the like, in an inert organic solvent such as acetonitrile, dichloromethane, ether, tetrahydrofuran, or the like.

Phosphinyl-acetic or propionic acid derivatives of formula III can be prepared using known procedures; see, for example, U.S. Pat. No. 4,168,267, issued Sept. 18, 1979. Phospholanes of formula VII can be prepared following the procedures described in Zh. Obsh. Kim., 37:411 (1967) and Zh. Obsh. Kim., 38:288 (1968).

The amino acid esters of formula II are known or are readily obtainable using known esterification techniques which are illustrated in the examples.

Additional processes for preparing the compounds of this invention will be apparent to the practitioner of this invention. For example, the carboxyl group of an amino acid having the formula

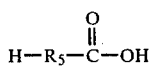

VIII can be protected, e.g., by conversion to an amine salt, or a 2-hydroxyethyl or diphenylmethyl ester, reacted with a phosphinyl-acetic or propionic acid of formula III, and then deprotected to yield a product of formula VI.

Esterification of a product of formula VI using art-recognized procedures yields the corresponding product of formula IV.

An alternative procedure for preparing the compounds of this invention wherein $R_2$ is alkyl, arylalkyl or

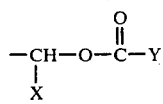

and $R_4$ is hydrogen comprises first alkylating the corresponding compound of formula V wherein $R_4'$ is benzhydryl or t-butyl, and then subjecting the resulting compound to ester cleavage with trifluoroacetic acid and anisole or with other art-recognized reagents.

The compounds of formula I (wherein $-R_5-COO$ is a residue of an amino acid other than glycine) exist in diasteromeric forms or in racemic mixtures thereof; all are within the scope of this invention. The L-isomers are preferred.

The compounds of this invention wherein at least one of $R_2$ or $R_4$ is hydrogen, form basic salts with various inorganic and organic bases which are also within the scope of the invention. Such salts include ammonium salts, alkali metal salts like lithium, sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

The following examples are specific embodiments of this invention.

EXAMPLE 1

N-[[Ethoxy(4-phenylbutyl)phosphinyl]acetyl]-L-tyrosine, methyl ester 1,1'-Carbonyldiimidazole (0.56 g) was added portionwise to a cooled (0° C.) solution of [ethoxy(4-phenylbutyl)phosphinyl]acetic acid (0.98 g) in 70 ml of acetonitrile. This reaction mixture was stirred under argon at 0° C. for 1.5 hours. The HCl salt of L-tyrosine methyl ester (0.8 g) was dissolved in methanol and neutralized with triethylamine (0.35 g). This solution was concentrated in vacuo, dissolved in 10 ml of warm acetonitrile and added dropwise to the above solution of activated phosphinic acid ester sidechain. The reaction was stirred overnight under argon and then concentrated in vacuo. A solution of the pot residue in dichloromethane was washed (H₂O, aqueous NaHCO₃, brine), dried (MgSO₄) and filtered to yield 1.4 g of N-[[ethoxy(4-phenylbutyl)phosphinyl]acetyl]-L-tyrosine, methyl ester.

EXAMPLE 2

N-[[Hydroxy(4-phenylbutyl)phosphinyl]acetyl]-L-tyrosine, methyl ester

Trimethylsilylbromide (0.5 ml) was added to a cooled solution of N-[[ethoxy(4-phenylbutyl)-phosphinyl]acetyl]-L-tyrosine, methyl ester (1.4 g; see example 1) in 50 ml of dichloromethane. This was stirred under argon for 2 days and then concentrated in vacuo. The residue was dissolved in 150 ml of ethyl acetate, washed (10% aqueous NaH₂PO₄, brine) and dried (MgSO₄). Product was separated from starting material by extracting the ethyl acetate solution with three portions of 25% aqueous NaHCO₃. The bicarbonate solution was acidified with 10% aqueous HCl and extracted with two 100 ml portions of ethyl acetate containing 5 ml of isopropanol. This was dried with MgSO₄, filtered and concentrated in vacuo to yield 0.94 g of analytical product.

Calc. for $C_{22}H_{28}NO_6P$: C, 60.96; H, 6.51; N, 3.23; P, 7.15, for $C_{22}H_{28}NO_6P\cdot 0.5\ H_2O$: C, 59.72; H, 6.61; N, 3.17; P, 7.0 Found: C, 59.56; H, 6.27; N, 3.00; P, 6.7.

EXAMPLE 3

N-[[Hydroxy(4-phenylbutyl)phosphinyl]acetyl]-L-tyrosine

N-[[Hydroxy(4-phenylbutyl)phosphinyl]acetyl]-L-tyrosine, methyl ester (0.86 g; see example 2) was dissolved in 10 ml of methanol. Sodium hydroxide (0.24 g) in 7 ml of water was added and this was stirred at room temperature for 4 hours. At the end of this time period the pH was 10. Methanol was evaporated off and the reaction mixture was diluted to 20 ml with water, filtered through a Millipore filter, and the filtrate was acidified with 10% KHSO₄. The aqueous solution was saturated with salt, extracted with ethyl acetate, dried (MgSO₄), filtered and concentrated in vacuo to yield 0.5 g of analytical material.

Calc. for $C_{21}H_{26}NO_6P$: C, 60.28; H, 6.02; N, 3.35; P, 7.4, for $C_{21}H_{26}NO_6P\cdot 0.25\ H_2O$: C, 59.64; H, 6.08; N, 3.31; P, 7.3, Found: C, 59.44; H, 6.13; H, 3.05; P, 7.1.

EXAMPLE 4

$N^2$-[[Ethoxy(4-phenylbutyl)phosphinyl]acetyl]-L-arginine

To a solution of 5 g of [ethoxy(4-phenylbutyl)phosphinyl]acetic acid in 132 ml of dry dimethylformamide (DMF) at room temperature under nitrogen was added 2.9 g of 1,1'-carbonyldiimidazole (CDI). After one hour at room temperature, the reaction mixture was treated with 3.1 g of L-arginine added as a solid in one portion. After stirring the reaction mixture overnight under nitrogen, the DMF was removed in vacuo and the crude reaction mixture was dissolved in water, acidified to pH 2 with concentrated HCl and extracted with ether. Work-up of the ether layer gave 1.7 g of the starting acid. The desired product was isolated by application of the acidified aqueous extract to an ion exchange column (AG50W-X2) (H+)) prepared in water. Initial elution with water removed the acidic material. When the pH returned to near neutral a gradient from water to 0.07 M pH 6.5 pyridine-acetic acid buffer was run. The Sakaguchi positive fractions were pooled and lyophilized to afford 2.1 g of product. This material was finally purified on about 500 ml of Sephadex LH-20 resin in water to afford 1.9 g of the title compound, melting point 55°–65° C.; $[\alpha]_D$ negligible.

Calc'd. for 1.4 H$_2$O: C, 51.58; H, 7.75; N, 12.03; P, 6.65, Found: C, 51.49; H, 7.30; N, 11.95; P, 6.70.

EXAMPLE 5

N$^2$-[[Hydroxy(4-phenylbutyl)phosphinyl]acetyl]-L-arginine

A solution of N$^2$-[[ethoxy(4-phenylbutyl)-phosphinyl]acetyl]-L-arginine (652 mg; see example 4) in 15 ml of 4 N hydrogen bromide/acetic acid was kept at room temperature in a stoppered flask overnight. The reaction mixture was then purged with a stream of nitrogen and repeatedly treated with water and concentrated on a rotary evaporator. Lyophilization afforded 1.04 g of crude product. Chromatography on the weakly acidic carboxymethyl cellulose CM-52(H+) resin yielded material which still had 0.75 equivalents of HBr as indicated by microanalysis. The title compound was finally obtained pure by passage through ion exchange resin (AG50W-X2 (H+)) eluted first with water to remove HBr, then finally with 5% aqueous pyridine to yield a total of 178 mg of product as a white solid after lyophilization. The product was a 0.7 H$_2$O solvate.

EXAMPLE 6

N-[[(2-Phenylethyl)(phenylmethoxy)phosphinyl]-acetyl]-L-tryptophan, phenylmethyl ester

[(2-Phenylethyl)(phenylmethoxy)phosphinyl]-acetic acid (3.2 g) and 1,1'-carbonyldiimidazole (1.6 g) were stirred in 50 ml of dry acetonitrile in an ice bath for 1 hour. The free base of L-tryptophan, benzyl ester derived from 4.8 g of the hydrochloride salt (from ether/NaHCO$_3$) was added in a little acetonitrile. After stirring at 0° C. for 1 hour, the mixture was allowed to stand at room temperature overnight, taken up in ether, washed with 5% NaHSO$_4$, brine, saturated NaHCO$_3$, brine (2 times), dried (Na$_2$SO$_4$), and evaporated to dryness yielding 5.7 g of product. This material was flash chromatographed on LP-1 silica gel (400 ml) eluted with ethyl acetate and yielded 3.6 g of product as a slightly colored oil.

Analysis calc'd for C$_{35}$H$_{31}$N$_2$O$_5$P: C, 70.69; H, 5.93; N, 4.71; P, 5.21, Found: C, 70.55; H, 5.98; N, 4.65; P, 5.28.

EXAMPLE 7

N-[[Hydroxy-(2-phenylethyl)phosphinyl]acetyl]-L-tryptophan, ammonia salt

N-[[(2-Phenylethyl)(phenylmethoxy)phosphinyl]-acetyl]-L-tryptophan, phenylmethyl ester (3.3 g; see example 6) was dissolved in methanol, and lithium hydroxide monohydrate (0.466 g) dissolved in a little water was added. The mixture was stirred at room temperature for 2 hours; 10% palladium on charcoal (1 g) was added and the mixture hydrogenated at 1 atmosphere for 2 hours. The catalyst was filtered off through Celite and the filtrate evaporated to dryness. The residue was dissolved in water, passed through a Millipore filter, and lyophilized yielding 2.1 g of product, melting point >350° C., $[\alpha]_{RT}^D+3.9°[1,H_2O]$.

Analysis calc'd for C$_{21}$H$_{21}$N$_2$O$_5$PLi$_2$.3H$_2$O: C, 52.51; H, 5.67; N, 5.83; P, 6.45; Li, 2.89. Found: C, 52.44; H, 5.64; N, 5.64; P, 6.40; Li, 3.1.

Electrophoresis showed this material to have two components. It (300 mg) was chromatographed on DEAE sephadex (60 ml) (OH form, pH 7.4) eluted with a NH$_4$HCO$_3$ gradient (0.005 to 0.5 M). Pure fractions (one component by electrophoresis) were combined and evaporated. The residue was dissolved in water, Millipore filtered and lyophilized two times yielding 0.29 g of product, $[\alpha]_{RT}^D+3°[0.5, H_2O]$.

Analysis calc'd for C$_{21}$H$_{23}$N$_2$O$_5$P(NH$_3$, H$_2$O): C, 56.12; H, 6.28; N, 9.35; P, 6.87, Found: C, 55.95; H, 5.90; N, 9.43; P, 6.60.

EXAMPLES 8–24

Following the procedure of examples 4 and 5, but starting with the compound listed in column I in place of L-arginine, yields the compound listed in column II. In example 21, it is necessary to use a protected lysine derivative.

| | Column I | Column II |
|---|---|---|
| 8. | L-alanine | N$^2$—[[hydroxy(4-phenylbutyl)-phosphinyl]acetyl]-L-alanine |
| 9. | L-leucine | N$^2$—[[hydroxy(4-phenylbutyl)-phosphinyl]acetyl]-L-leucine |
| 10. | N—methyl-L-leucine | N$^2$—[[hydroxy(4-phenylbutyl)-phosphinyl]acetyl]-N—methyl-L-leucine |
| 11. | glycine | N$^2$—[[hydroxy(4-phenylbutyl)-phosphinyl]acetyl]glycine |
| 12. | L-valine | N$^2$—[[hydroxy(4-phenylbutyl)-phosphinyl]acetyl]-L-valine |
| 13. | L-isoleucine | N$^2$—[[hydroxy(4-phenylbutyl)-phosphinyl]acetyl]-L-isoleucine |
| 14. | L-phenylalanine | N$^2$—[[hydroxy(4-phenylbutyl)-phosphinyl]acetyl]-L-phenylalanine |
| 15. | L-serine | N$^2$—[[hydroxy(4-phenylbutyl)-phosphinyl]acetyl]-L-serine |
| 16. | L-threonine | N$^2$—[[hydroxy(4-phenylbutyl)-phosphinyl]acetyl]-L-threonine |
| 17. | L-cysteine | N$^2$—[[hydroxy(4-phenylbutyl)-phosphinyl]acetyl]-L-cysteine |
| 18. | L-methionine | N$^2$—[[hydroxy(4-phenylbutyl)-phosphinyl]acetyl]-L-methionine |
| 19. | L-aspartic acid | N$^2$—[[hydroxy(4-phenylbutyl)-phosphinyl]acetyl]-L-aspartic acid |
| 20. | L-glutamic acid | N$^2$—[[hydroxy(4-phenylbutyl)-phosphinyl]acetyl-L-glutamic acid |
| 21. | ε-t-butoxycarbonyl-L-lysine | N$^2$—[[hydroxy(4-phenylbutyl)-phosphinyl]acetyl]-L-lysine |
| 22. | L-asparagine | N$^2$—[[hydroxy(4-phenylbutyl)-phosphinyl]acetyl]-L-asparagine |
| 23. | L-glutamine | N$^2$—[[hydroxy(4-phenylbutyl)-phosphinyl]acetyl]-L-glutamine |
| 24. | L-histidine | N$^2$—[[hydroxy(4-phenylbutyl)-phosphinyl]acetyl]-L-histidine |
| 25. | L-norvaline | N$^2$—[[hydroxy(4-phenylbutyl)-phosphinyl]acetyl]-L-norvaline |
| 26. | L-norleucine | N$^2$—[[hydroxy(4-phenylbutyl)-phosphinyl]acetyl]-L-norleucine |

EXAMPLE 27

N-[[[(2,2-Dimethyl-1-oxopropoxy)methoxy](4-phenylbutyl)phosphinyl]acetyl]-L-phenylalanine (A) [Hydroxy(4-phenylbutyl)phosphinyl]acetic acid, phenylmethyl ester A solution of benzyl chloroformate (1.8 ml, 12.6 mmol) in 5 ml of dry tetrahydrofuran was added dropwise to a solution of [hydroxy(4-phenylbutyl)phosphinyl]acetic acid (2.55 g, 10 mmol) and triethylamine (2.0 ml, 14.5 mmol) in 30 ml of dry tetrahydrofuran at 0° C. After addition was complete, the mixture was stirred at 0° C. for 30 minutes and at room temperature for 1 hour. The mixture was positioned between ethyl acetate and 5% KHSO$_4$ and the ethyl acetate layer was evaporated to a residue. The residue was taken up in aqueous NaHCO$_3$, washed with ethyl acetate, and the aqueous solution acidified to pH 1 and extracted with ethyl acetate. The extracts were dried (Na$_2$SO$_4$) and evaporated to give the crude product which was triturated with pentane to yield a solid, melting point 64°-67° C. (3.30 g).

(B)

[[(2,2-Dimethyl-1-oxopropoxy)methoxy](4-phenylbutyl)phosphinyl]acetic acid, phenylmethyl ester

[Hydroxy(4-phenylbutyl)phosphinyl]acetic acid, phenylmethyl ester (3.30 g, 9.5 mmol) was taken up in 10 ml of dry dimethylformamide and treated with triethylamine (2.7 ml, 9.5 mmol) and chloromethyl pivalate (2.8 ml, 19.4 mmol) and stirred at room temperature under argon for 16 hours. The mixture was diluted with ethyl acetate and washed with water, 5% KHSO$_4$, and saturated NaHCO$_3$, then dried (Na$_2$SO$_4$) and evaporated to a residue which was purified by flash chromatography on silica gel using ethyl acetate-hexane eluant to yield the title diester (3.65 g, 83%) as a colorless oil. TLC R$_F$(ethyl acetate/hexane, 1:1)=0.39.

(C)

[[(2,2-Dimethyl-1-oxopropoxy)methoxy](4-phenylbutyl)phosphinyl]acetic acid

[[(2,2-Dimethyl-1-oxopropoxy)methoxy](4-phenylbutyl)phosphinyl]acetic acid, phenylmethyl ester (2.95 g, 6.4 mmol) in 75 ml of ethyl acetate was hydrogenated at 48 psi over 10% palladium on charcoal catalyst (0.4 g) for 1 hour. The mixture was filtered through Celite and evaporated to dryness to give the title acid as a colorless oil which solidified to a solid, melting point 48°-50° C.

(D)

[[(2,2-Dimethyl-1-oxopropoxy)methyl](4-phenylbutyl)phosphinyl]acetic acid, N-hydroxy succinimide ester

[[(2,2-Dimethyl-1-oxopropoxy)methoxy](4-phenylbutyl)phosphinyl]acetic acid (2.22 g, 6 mmol), N-hydroxy succinimide (0.69 g, 6 mmol), and dicyclohexylcarbodiimide (1.24 g, 6 mmol) were dissolved in dry tetrahydrofuran at 0° C. The mixture was stirred overnight at room temperature, filtered and the filtrate concentrated in vacuo to an oily residue which was triturated with diisopropyl ether, yielding a solid, melting point 102°-105° C. (2.1 g).

(E)

N-[[[(2,2-Dimethyl-1-oxopropoxy)methoxy]-(4-phenylbutyl)phosphinyl]acetyl]-L-phenylalanine L-Phenylalanine (1.65 g, 10 mmol), triethylamine (2.8 ml, 20 mmol) and [[(2,2-dimethyl-1-oxopropoxy)methoxy]-(4-phenylbutyl)phosphinyl]acetic acid, N-hydroxy succinimide ester (4.67 g, 10 mmol) are dissolved in 50 ml of dry dimethylformamide and stirred overnight under argon at room temperature. The reaction mixture is partitioned between dichloromethane and 5% KHSO$_4$, and the organic layer is washed with water and brine and then dried and evaporated to yield the desired product.

EXAMPLES 28-34

Following the procedure of example 27, but substituting the compound in column I for [hydroxy(4-phenylbutyl)phosphinyl]acetic acid, the compound in column II for chloromethyl pivalate and the compound in column III for L-phenylalanine, yields the compound listed in column IV.

| | Column I | Column II | Column III | |
|---|---|---|---|---|
| 28. | [hydroxy(4-phenylbutyl)]-phosphinyl acetic acid | chloromethyl pivalate | L-alanine | N—[[[(2,2-dimethyl)-oxopropoxy)-methoxy](4-phenylbutyl)phosphinyl]acetyl]-L-alanine |
| 29. | [hydroxy(4-phenylbutyl)-phosphinyl]acetic acid | acetic acid, 1-chloroethyl ester | L-phenylalanine | N—[[[1-(acetyloxy)ethoxy](4-phenylbutyl)phosphinyl]acetyl]-L-phenylalanine |
| 30. | [hydroxy(2-phenylethyl)-phospninyl]acetic acid | isobutyric acid, chloromethyl ester | L-tryptophan | N—[[[(2-Methyl-2-oxopropoxy)methoxy-4-phenylbutyl)phosphinyl]acetyl]-L-tryptophan |
| 31. | [hydroxy(4-phenylbutyl)-phosphinyl]acetic acid | carbonic acid, ethyl chloromethyl diester | L-phenylalanine | N—[[[(ethoxycarbonyloxy)methoxy]-(4-phenylbutyl)phosphinyl]acetyl]-L-phenylalanine |
| 32. | [hydroxy(octyl)phosphinyl]acetic acid | propionic acid, 1-chloroethyl | L-tyrosine | N—[[octyl[1-(1-oxopropoxy)ethoxy]-phosphinyl]acetyl]-L-tyrosine |
| 33. | [hexyl(hydroxy)phosphinyl]acetic acid | 1-chloroethyl pivalate | L-methionine | N—[[[1,(2,2-dimethyl-1-oxopropoxy)-ethoxy](hexyl)phosphinyl]acetyl]-L-methionine |
| 34. | [hydroxy(4-phenylbutyl)-phosphinyl]-α-methyl-propionic acid | 1-chloroethyl pivalate | L-arginine | N—[2-methyl-1-oxo-[[1-(1-oxopropoxy)-ethoxy](4-phenylbutyl)phosphinyl]-propyl]-L-arginine |

What is claimed is:
1. A compound having the formula

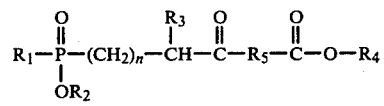

or a salt thereof, wherein

R$_1$ is alkyl, aryl, arylalkyl, cycloalkyl, or cycloalkyl(alkyl);

R$_2$ and R$_4$ each is independently hydrogen, alkyl, arylalkyl or

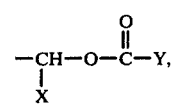

wherein X is hydrogen, alkyl, or phenyl and Y is hydrogen, alkyl, phenyl or alkoxy, or together X and Y are —(CH$_2$)—$_2$, —(CH$_2$)$_3$—, —CH=CH— or

R₃ is hydrogen or alkyl;

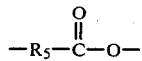

is a residue of an amino acid selected from the group consisting of glycine, alanine, valine, norvaline, leucine, N-methylleucine, norleucine, isoleucine, phenylalanine, tyrosine, serine, threonine, cysteine, methionine, aspartic acid, glutamic acid, arginine, lysine, asparagine, glutamine, histidine, or tryptophane; and n is 0 or 1;

wherein the amino acid residue

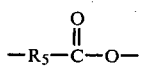

is linked to the adjacent carbonyl group by an amide bond.

2. A compound in accordance with claim 1 wherein n is 1.

3. A compound in accordance with claim 1 wherein R₂ and R₄ each is hydrogen.

4. A compound in accordance with claim 1 wherein one of R₂ and R₄ is hydrogen and the other is

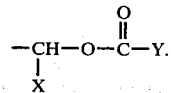

5. The compound in accordance with claim 1 N-[[ethoxy(4-phenylbutyl)phosphinyl]acetyl]-L-tyrosine, methyl ester.

6. The compound in accordance with claim 1 N-[[hydroxy(4-phenylbutyl)phosphinyl]acetyl]-L-tyrosine, methyl ester.

7. The compound in accordance with claim 1 N-[[hydroxy(4-phenylbutyl)phosphinyl]acetyl]-L-tyrosine.

8. The compound in accordance with claim 1 N²-[[ethoxy(4-phenylbutyl)phosphinyl]acetyl]-L-arginine.

9. The compound in accordance with claim 1 N²-[[hydroxy(4-phenylbutyl)phosphinyl]acetyl]-L-arginine.

10. The compound in accordance with claim 1 N-[[(2-phenylethyl)(phenylmethoxy)phosphinyl]-acetyl]-L-tryptophan, phenylmethyl ester.

11. The compound in accordance with claim 1 N-[[hydroxy(2-phenylethyl)phosphinyl]acetyl]-L-tryptophan, ammonia salt.

* * * * *